United States Patent [19]
Pilla et al.

[11] Patent Number: 5,723,001
[45] Date of Patent: Mar. 3, 1998

[54] APPARATUS AND METHOD FOR THERAPEUTICALLY TREATING HUMAN BODY TISSUE WITH ELECTROMAGNETIC RADIATION

[75] Inventors: Arthur A. Pilla, Ridgewood, N.J.; Viswanathan Iyer, Deerfield Beach; Walter Leonard Wasserman, Boca Raton, both of Fla.

[73] Assignee: Electropharmacology, Inc., Pompano Beach, Fla.

[21] Appl. No.: 642,213

[22] Filed: May 6, 1996

Related U.S. Application Data

[63] Continuation of Ser. No. 501,271, Jul. 12, 1995, abandoned, which is a continuation of Ser. No. 257,281, Jun. 9, 1994, abandoned.

[51] Int. Cl.$^6$ ............................................. A61N 1/32
[52] U.S. Cl. ............................................. 607/68
[58] Field of Search ............................ 607/2, 68, 71, 607/72, 73, 74, 154, 155

[56] References Cited

U.S. PATENT DOCUMENTS 4,197,851  4/1980  Fellus ........................................ 607/71
4,338,945  7/1982  Kosugi et al. .............................. 607/73

FOREIGN PATENT DOCUMENTS

| 0608693 | 11/1960 | Canada ................................ 607/68 |
| 0543152 | 5/1993 | European Pat. Off. ................ 607/73 |
| 0970276 | 9/1958 | Germany .............................. 607/72 |
| 0604107 | 6/1948 | United Kingdom .................. 607/71 |
| 2162066 | 1/1986 | United Kingdom .................. 607/73 |
| 3001742 | 5/1983 | WIPO .................................. 607/68 |

*Primary Examiner*—William E. Kamm
*Attorney, Agent, or Firm*—Jones, Day, Reavis & Pogue

[57] ABSTRACT

Broad spectral density bursts of electromagnetic waveforms having a frequency in the range of one to one hundred megahertz, with 100 to 100,000 pulses per burst, and with a burst-repetition rate of 0.01 to 1000 Hertz, are selectively applied to a living body (or to living cells). The voltage-amplitude envelope of each pulse burst is a function of a random, irregular, or other like variable effective to provide a broad spectral density within the burst envelope.

34 Claims, 5 Drawing Sheets

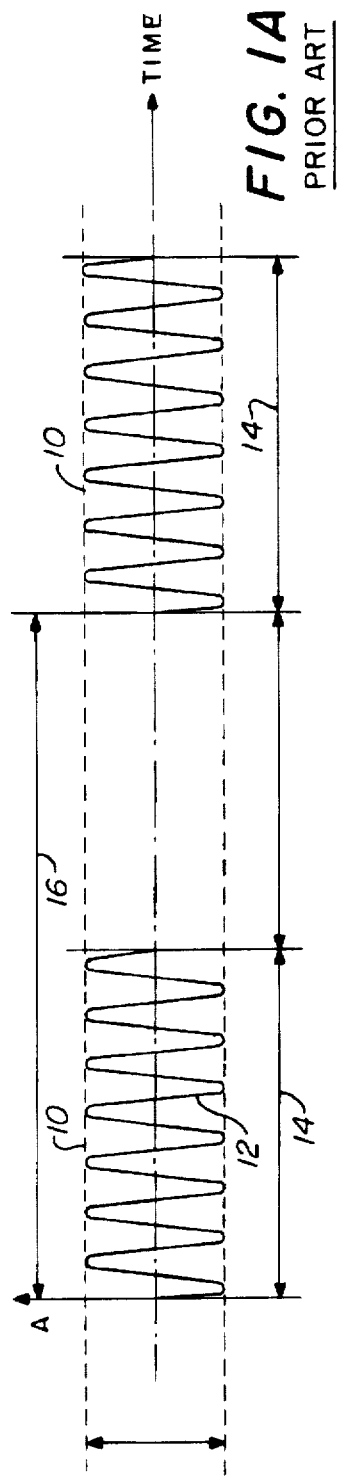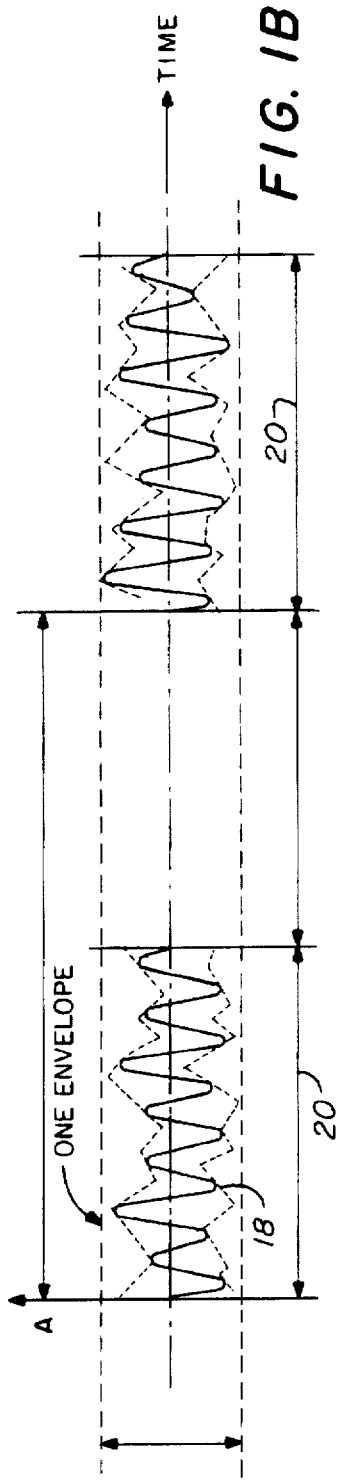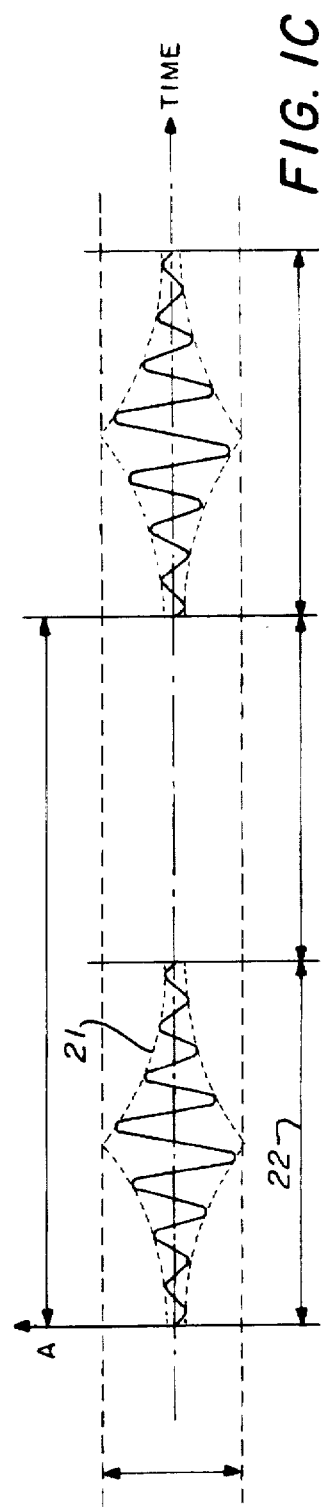

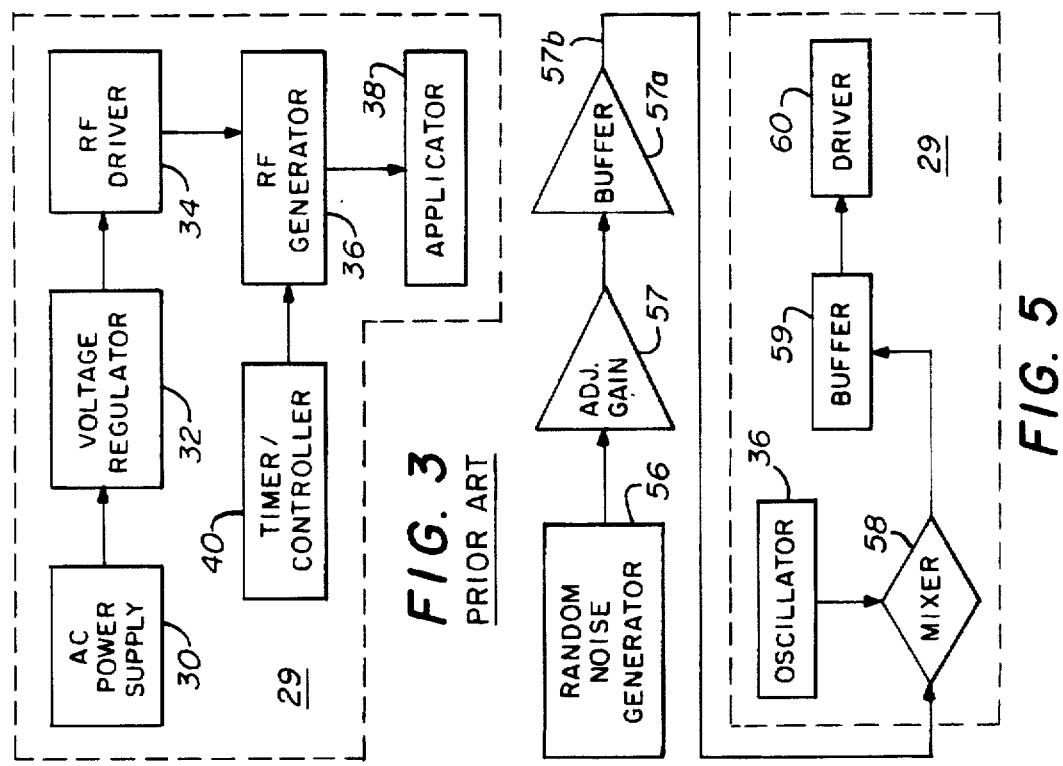
FIG. 3 PRIOR ART
FIG. 5
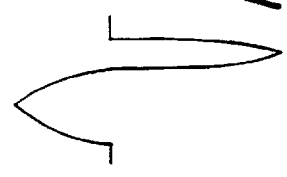
FIG. 2A
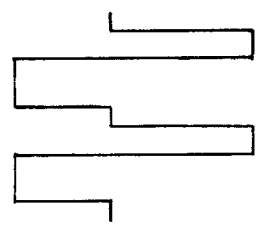
FIG. 2C
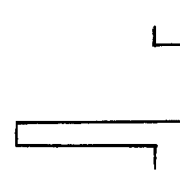
FIG. 2B
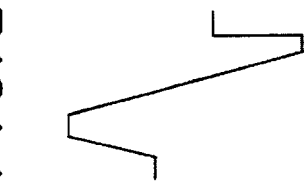
FIG. 2E
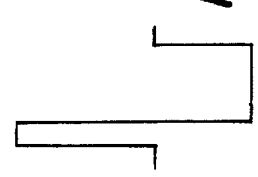
FIG. 2D
FIG. 2F

APPARATUS AND METHOD FOR THERAPEUTICALLY TREATING HUMAN BODY TISSUE WITH ELECTROMAGNETIC RADIATION

This application is a continuation of application Ser. No. 501,271, filed Jul. 12, 1995, now abandoned, which is a continuation of application Ser. No. 08/257,281, filed Jun. 9, 1994, and now abandoned.

BACKGROUND OF THE INVENTION

This invention relates to the treatment of living tissues and/or cells by altering their interaction with their magnetic environment. The invention also relates to a method of modification of cellular and tissue growth, repair, maintenance, and general behavior by the application of encoded electromagnetic information. More particularly, this invention provides for the application, by surgically non-invasive reactive coupling, of highly specific electromagnetic signal patterns to one or more body parts.

This technology experienced a relatively slow growth during the initial phase of its development which, generally, corresponded to the period of 1930 through 1975. The prior art reflective of work in this period is typified by French Patent No. 748,828 (1933) to Siemens which shows the use of a variable width plate capacitor in an applicator head for use in electromagnetic therapy; and U.S. Pat. No. 2,130,758 (1938) to Rose which teaches the design of electrodes for use in a diathermy machine. Accordingly, diathermy, which provides heat to human tissue, represents a precursor to the present invention.

Over time and, particularly, by about 1962, it was established that the effects of diathermy could be achieved by non-thermal means. Such effects are reflected in U.S. Pat. Nos. 3,043,310 (1964) and 3,181,535 (1965) both to Milinowski, who used the expression "athermapeutic", meaning non-thermal. Milinowski's "athermapeutic" apparatus utilized pulsed bursts of a high-frequency sinusoidal wave in the range of 27 megahertz, and he stated that an athermapeutic apparatus utilizing pulsed bursts of high-frequency radiation will produce greater beneficial results than continuous-wave diathermy, i.e., without such pulsing of the waveform, particularly, in that heat tolerance is no longer a factor.

The technology of clinically using pulsed radio-frequency fields (PRF) in the megahertz range first appeared in U.S. Pat. No. 3,270,746 (1966) and No. 3,329,149 (1967) both to Kendall, and further in U.S. Pat. No. 3,952,751 (1976) to Yarger, entitled High Performance Electrotherapeutic Apparatus.

The use of most so-called low frequency EMF has been with relationship to applications of repair or healing of bone. As such, the EMF waveform and current orthopedic clinical use thereof contains relatively low frequency components and is of a very low power, inducing maximum electrical fields in the millivolts per centimeter (mV/cm) range at frequencies under five kilohertz. The origins of such a bone repair signal began with the early work of Becker, Yasuda, Brighton and Bassett which considered that an electrical pathway may constitute a means through which bone can adoptively respond to such an EMF input. This work was followed by a linear physicochemical approach taken by Pilla (one of the within inventors) who employed an electrochemical model of the cell membrane to predict a range of EMF waveform patterns for which bioeffects might be expected. This approach was based upon an assumption that the cell membrane was the most likely EMF target. This effort became one of finding the range of waveform parameters for which an induced electric field could couple to electrochemical, i.e., voltage-dependent kinetics, at the cellular surface. Extension of this linear model involved Lorentz force considerations which eventually led to the suggestion that the magnetic field alone could be considered the dominant stimulus in EMF/PRF electrotherapy. These thoughts resulted in ion resonance and quantum theories that predicted benefits from combined AC and DC magnetic field effects at very low frequency ranges. This area of research is reflected in U.S. Pat. Nos. 4,105,017, 4,266,532 and No. 4,266,533, all to Ryaby, et al.

As above noted, a PRF signal derived from a 27 MHz continuous sine wave used for deep tissue healing is known in the prior art of diathermy and its above referenced non-thermal successors thereto. A pulsed successor of the diathermy signal was originally reported as an electromagnetic field capable of eliciting a non-thermal biological effect in the treatment of infections by Ginzberg. Since that original work, PRF therapeutic applications have been reported for the reduction of posttraumatic and post-operative pain and edema in soft tissues, wound healing, burn treatment, and nerve regeneration. The application of EMF for the resolution of traumatic edema has become increasingly used in recent years. Results to date using PRF in animal and clinical studies suggest that edema may be measurably reduced from such electrophysical stimulus.

Two general mechanisms have been proposed for the effect of PRF on edema. The first suggests that EMF affects sympathetic outflow, including vasoconstriction, which restricts movement of blood constituents from vascular to extravascular compartments at the injury site. The second proposes that the passage of electrical current through the tissue displaces the negatively charged plasma proteins found in the interstitium of the traumatized tissue. This increased mobility, it is suggested, operates to accelerate protein uptake by the lymphatic capillaries, thereby increasing lymphatic flow which is an established mechanism for extracellular fluid uptake resultant from traumatic edema.

The within invention is based upon biophysical and animal studies which attribute the effect of cell-to-cell communication on the sensitivity of tissue structures to induced voltages and associated currents. These studies have established that prior art considerations of EMF dosimetry have not taken into account the dielectric properties of tissue structure (as opposed to the properties of isolated cells). The implications thereof are that a proper, i.e., an efficient, reactive coupling of a PRF signal to tissue has not heretofore been effected in the art of record. This art, as is typified in the efforts of the last ten years relative to high frequency PRF, is reflected in U.S. Pat. Nos. 4,454,882 (1984) to Fellus, entitled Electrotherapeutic Apparatus; No. 4,674,482 (1987) to Waltonen, entitled Pulsed Electromagnetic Field Therapy Device; No. 4,998,532 (1990) to Griffith entitled Portable Electro-Therapy System; and No. 5,014,699 (1991) to Pollack et al, entitled Electromagnetic Method and Apparatus for Healing Living Tissue.

In recent years, the clinical use of non-invasive PRF at radio frequencies has consisted of the use of pulsed bursts of a 27.12 MHz sinusoidal wave, each such pulse burst typically exhibiting a width of sixty five microseconds and containing approximately 1,700 sinusoidal cycles per burst, and with various burst repetition rates. This art is reflected in such clinical therapeutic devices as the SofPulse apparatus available from Magnetic Resonance Therapeutics, Inc., now Electropharmacology, Inc., of Pompano Beach, Fla.

The present invention is based upon the hypothesis that by providing to the pulse burst envelope a higher spectral density, the effect of therapy upon the relevant dielectric pathways, such as, cellular membrane receptors, ion binding to cellular enzymes, and general transmembrane potential changes, could be enhanced. In other words, the instant invention developed from the concept that, by the use of a substantially single voltage amplitude envelope with each PRF burst, one was limiting the frequency components that could couple to the relevant dielectric pathways in cells and tissue and, accordingly, that by increasing the number of frequency components transmitted to relevant cellular pathways, one would gain access to a larger range of biophysical phenomena applicable to known healing mechanisms, including those described above, i.e., relevant sympathetic blood flow at injury sites and acceleration of protein uptake by lymphatic capillaries. The instant invention is, accordingly, the result of the discovery by the inventors that by applying a random, or other high spectral density envelope, to the pulse burst envelope of mono or bi-polar rectangular or sinusoidal pulses of a relatively high voltage (below a tissue-induced motor-response level in the order of volts per centimeter (V/cm)), a greater effect could be accomplished on biological healing processes applicable to both soft and hard tissues.

As a secondary, but practical, consequence of the approach of the instant invention, it has been discovered that by applying a high spectral density voltage envelope as the modulating or pulse-burst defining parameter, the power requirement for such amplitude modulated pulse bursts can be significantly lower than that of an unmodulated pulse burst containing pulses within the same frequency range; this is due to a substantial reduction in the duty cycle within each of the repetitive burst trains brought about by the imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement, are achieved.

SUMMARY OF THE INVENTION

The present invention relates to a therapeutically beneficial method of and apparatus for non-invasive pulsed radio frequency electromagnetic treatment for purposes of repair and growth of living tissue. This beneficial method operates to selectively change the bioelectromagnetic environment associated with the cellular and tissue environment through the use of electromagnetic means such as PRF generators and applicator heads therefore as are known in the art. The inventive method more particularly includes the provision of a flux path, to a selectable body region, of a succession of megahertz EMF pulses having a minimum width characteristic of at least 0.01 microseconds in a pulse burst envelope having between 100 and 10,000 pulses per burst, in which a voltage amplitude envelope of said pulse burst is defined by a randomly varying parameter in which the instantaneous minimum amplitude thereof is not smaller than the maximum amplitude thereof by a factor of one ten thousandth. Further, the repetition rate of such pulse bursts may vary from 0.01 to 1000 Hertz. In special cases a mathematically definable parameter may be employed in lieu of said random amplitude envelope of the RF pulse bursts.

It is, accordingly, an object of the invention to provide an improved electromagnetic method of the beneficial treatment of living cells and tissue by the modulation of electromagnetically sensitive regulatory processes at the cell membrane and at junctional interfaces between cells.

It is another object to provide an electromagnetic treatment method of the above type having a broad band, high spectral density electromagnetic field.

It is a further object of the invention to provide a method of the above type in which amplitude modulation of the pulse burst envelope of the electromagnetic signal will induce coupling with a maximum number of relevant dielectric pathways in cells or tissues.

It is another object of the invention to provide an improved method of treatment of maladies of the bone and other hard tissue.

It is a still further object of the invention to provide an improved means of the treatment of edema and swelling of soft tissue.

It is another object to provide a means of repair of damaged soft tissue.

It is a yet further object to provide apparatus for use of an electromagnetic method of the character indicated, wherein operation of the apparatus can proceed at reduced power levels as compared to those of related methods known in electromedicine, with attendant benefits of safety, economics, portability, and reduced electromagnetic interference.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

FIG. 1A is a diagrammatic view of successive bursts of an unmodulated radio-frequency signal, in accordance with prior art.

FIGS. 1B to 1F are diagrammatic views of pulse bursts in accordance with the invention, showing random and irregularly modulated envelopes thereof.

FIG. 2, views a through f, illustrate representative variant pulse forms for iterative use within the pulse bursts shown in FIGS. 1B to 1F.

FIG. 3 is a block diagram of a representative prior art electronic system capable of furnishing the waveform shown in FIG. 1A.

FIG. 5 is a block diagram of a body-applicator driver circuit of the invention, featuring a random-noise generator and modulator for the pulsed-burst output of the circuit of FIG. 4.

DETAILED DESCRIPTION OF THE INVENTION

Figure 1D:
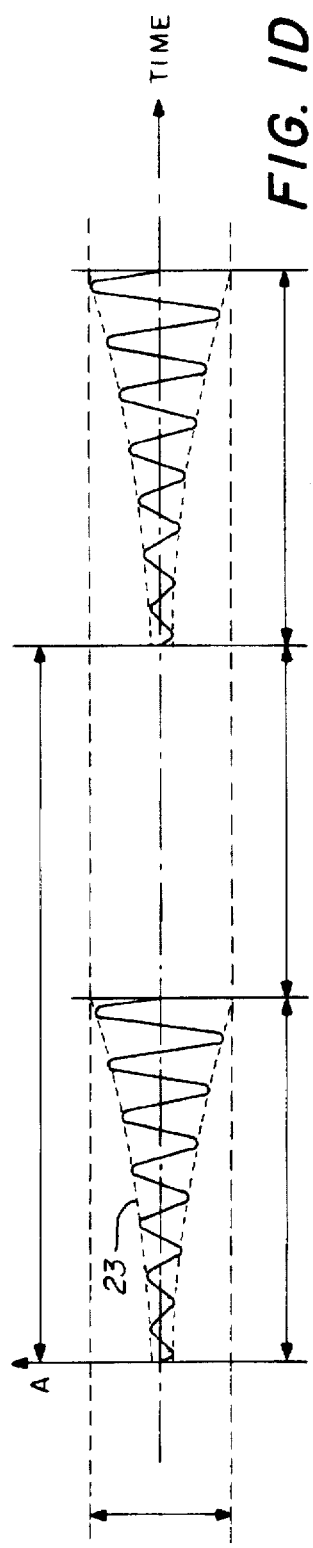

A starting point of understanding of the form of electromagnetic energy employed in the present electrotherapeutic method is that of a series of pulse bursts 10 of the type shown in FIG. 1A. Bursts of this type reflect state of the art use of uniform pulse burst envelope. Therein, it may be noted that a series of electromagnetic pulse bursts having a bipolar sinusoidal waveform 12 at a frequency in the range of one to one hundred megahertz are employed, a preferred frequency thereof being the regulatory approved wavelength of 27.12 megahertz. The peak amplitude (A) of the unmodulated pulse burst of FIG. 1A, measured in terms of induced voltage to tissue, is in the neighborhood of one volt per centimeter with a current of one milliamp per square centimeter. The duration 14 of each pulse burst width is about sixty five microseconds, with the range thereof being 10 to 1000 microseconds. The pulse width of each pulse within a pulse burst is, in the case of a sinusoidal wave, the inverse of the frequency of the waveform. Accordingly, in the waveform shown in FIG. 1A, the pulse width is about 0.037 microseconds. Thereby the number of cycles per pulse burst in the pulse burst 10 shown in FIG. 1A is about 1,750 pulses per burst. It is, however, to be understood that the number of cycles per pulse burst may fall anywhere in the range of 100 to 10,000. The pulse burst repetition rate 16 may be in the range of 0.01 to 1000 Hertz. Further, in the waveform shown in FIG. 1A the duty cycle within a pulse burst is typically in the range of two to three percent.

As such, the nature of the pulse train employed in the instant therapeutic method is that of very narrow pulse bursts that are delivered between extended non-burst periods. For example, the burst duration will, typically, be on the order of magnitude of one one-millionth of the pulse group repetition rate. Accordingly, it is to be appreciated that a principle of the present invention, which is carried forward from the prior art, is that very short pulse bursts, at high frequency and power, can prove highly effective in coupling to dielectric cellular pathways associated with healing processes.

As noted in the Background and Summary of the Invention, the inventive therapeutic method is based upon the discovery that, by increasing the spectral density of the burst envelope, one can broaden the range of relevant cellular impedance pathways to which the received energy of each PRF can couple. Thereby, the received dosimetry per unit of transmitted power can be enhanced. As is well known, the broadest frequency spectrum of any waveform is one in which the envelope thereof is random, inasmuch as random energy requires the greatest number of frequencies to simulate.

With reference to FIG. 1B there is shown a pulse burst having an envelope 18 in accordance with the present invention in which an envelope of randomly varying amplitude has been applied to the positive and negative amplitudes of the sinusoidal pulse bursts of the type shown in FIG. 1A. As is further set forth below, many means may be employed to provide such a random amplitude envelope this, for example, including random and digital noise generators.

With further reference to the signal of FIG. 1B, it is to be appreciated that the minimum amplitude A of each pulse burst 20 shall typically not be smaller than a factor of $10^{-4}$ than that of the maximum amplitude. All such amplitudes are measured at tissue level.

The use of a random amplitude for the pulse burst envelopes 18 shown in FIG. 1B has, as noted above, been selected by the within inventors to maximize the spectral density of the electromagnetic waveforms actually deliver at tissue level and, thereby, to increase the range of relevant dielectric pathways, these including lymphatic capillaries as a mechanism of increase of transmembrane cellular activity and extracellular fluid uptake. It is believed, that negatively charged plasma proteins typically found in the interstitium of tissue contribute to trauma. The invention is, therefore, based upon the discovery that broad band spectral density, e.g., consisting of more than one frequency and/or amplitude bursts of megahertz radio frequency waves (PRF/PRF) repeating, as to burst repetition rate, at frequencies between 0.01 and 1000 Hertz will generate induced coupling to tissue to thereby modulate a greater range of biophysical activities that are relevant to the healing process across ranges of soft and hard tissue trauma and disfunction, than is possible in the prior art. The instant invention, accordingly, teaches that a use of therapeutic signals having a spectral density, i.e., composed of a significantly wider frequency range, than that of prior art diathermy, SofPulse, and other known megahertz electrotherapeutic means, to thereby yield a more efficient coupling of the EMF signal to tissue than has heretofore been accomplished. As such, the highly irregular waveform envelope shown in FIG. 1B, consisting of bursts of high frequency RF sinusoidal waves, having the amplitude of the burst envelope modulated in a arbitrary, predetermined non-repeating fashion at between 0.01 and 1000 Hertz, will inductively couple to cellular pathways and thereby modulate biophysical activity in an advantageous fashion.

With reference to FIG. 1C, there is shown a second embodiment of the invention in which the pulse burst envelope 21 is irregular in the sense that it increases exponentially and then decreases exponentially within each pulse burst 22. Therein it is to be borne in mind that the maximum amplitude thereof may vary from $10^{-7}$ to $10^{0}$ and the minimum-to-maximum-to-minimum amplitude within each burst may not exceed a factor of $10^{-4}$.

With reference to FIG. 1D, there is shown a further embodiment of the invention which is irregular in the sense that an exponentially increasing symmetric positive/ negative envelope 23 follows those above described with reference to the waveform of FIGS. 1B and 1C.

Figure 1E:
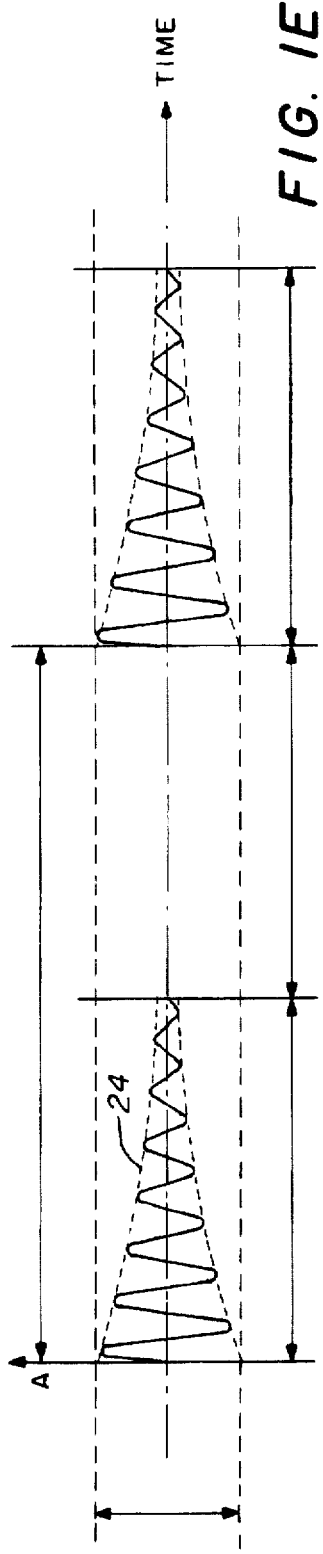

With reference to FIG. 1E there is shown another irregular-envelope embodiment of the instant invention, this essentially representing the inverse of that of FIG. 1D in which the amplitude of the envelope 24 decreases exponentially with time, rather than increasing.

Figure 1F:
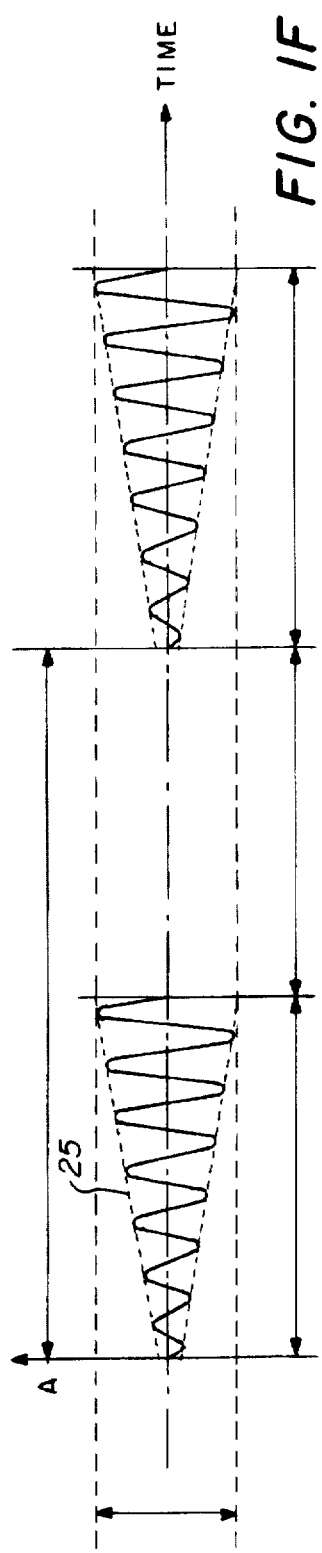

With reference to FIG. 1F there is shown a further irregular-envelope embodiment in which the amplitude of the envelope 25 of each pulse burst increases on a linear basis, as opposed to an exponential basis.

It is to be understood that, as long as the above set forth parameters of pulse width, pulse repetition rate, pulse burst width, pulse burst repetition rate, and ratio of greatest-to-least amplitude within the envelope for each burst is met, any mathematical function may be employed to define the envelope that is capable of widening the spectral density of the pulse burst. A further advantageous result thereof is that of reducing the intra-burst duty cycle and, therefore, the power requirement of the system by a factor of about 5.

With reference to FIG. 2, there are shown other intra-burst bi-polar waveforms that may be advantageously employed in cyclical repetition, in lieu of the sinusoidal waveform shown in FIG. 1A. Accordingly, some enhancement of effectiveness can be accomplished through the use of bipolar rectangular and/or jagged pulses. It is therefore within the scope of the invention to employ non-sinusoidal pulses if the other parametric constraints of the waveform and pulse burst set forth above are met. It is noted that the integrated areas of the positive and negative portions of each waveform are substantially equal.

Further, as noted in FIG. 2F, a multifrequency intra-burst waveform may be employed.

With reference to FIG. 3 there is shown in block diagram form a generic system 29 for providing waveforms of the type of FIG. 1A. The state of the art of circuits of this type is well established as is set forth in the assignee's co-pending application Ser. No. 07/889,504 (now U.S. Pat. No. 5,370,680) and, as well, in said above discussed references to Yarger, Kendall and Milinowski.

There is, more particularly, shown in the view of FIG. 3, an A/C power supply 30 which feeds into a voltage regulator 32 which in turn feeds an RF driver 34 which then feeds an RF generator 36. The output of generator 36 is applied to an applicator head 38 of an apparatus of the type shown in FIG. 9, while said generator, as to durations of given treatments, is controlled by a timer 40.

Figures 4, 6:
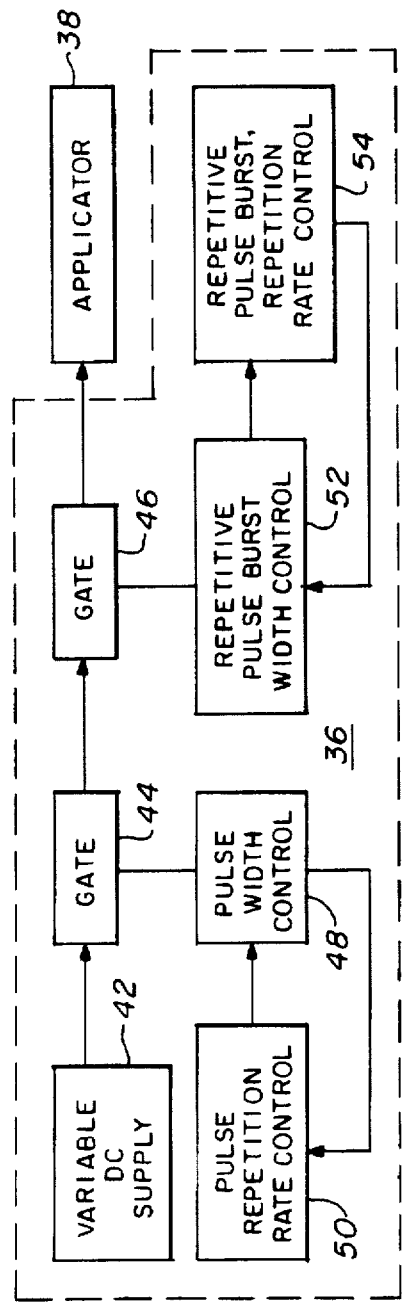
FIG. 4 is another block diagram (also in accordance with the prior art) with detail of the RF generator block of FIG. 3, showing the portion of the electronic system employed to generate a specific waveform of the type of FIG. 1A, with reference to the parameters of pulse width, pulse repetition rate, width of pulse burst and burst repetition rate.
FIG. 6 is a detailed circuit diagram of a random amplitude modulator corresponding generally to the subject matter of FIG. 5.

With reference to FIG. 4, there is shown, in block diagram format, those subsystems of RF generator 36 which define the appearance of an unmodulated PRF waveform of the type shown in FIG. 1A. More particularly, there is contained therein a variable DC supply 42 the output of which is fed into a first gate 44, the output of which is fed into a second gate 46, and the output of which is fed into said applicator head 38.

Further shown in FIG. 4 is means 48 for determining pulse width, i.e., the megahertz frequency control, and means 50 for pulse repetition rate control. As may be appreciated, in the use of a sinusoidal waveform of the type shown in FIG. 1A, control of pulse repetition rate and pulse width control constitute one and the same function. However, in the use of pulses of different geometry, as is set forth in FIGS. 2A through 2F pulse width control can constitute a separate function from that of control of pulse repetition rate. In FIG. 4 is also shown means 52 for pulse burst width control and means 54 for control of the repetition rate of the pulse bursts 20.

With reference to FIG. 5 there is shown at the right side thereof the generic generator system 29 of FIG. 3 to which there is added a random noise generator 56 which, in one embodiment of the invention, makes use of the zener breakdown phenomena of a PN junction transistor. Therein the transistor is reverse-biased and operated in the breakdown region. It has been established that this breakdown mechanism is random and it generates a high impedance random noise source. The output of this noise generator 56 is fed into an adjustable gain amplifier 57 and, therefrom, into a buffer 57a and into a mixer 58 to assure that the inputted random noise 59b is in fact random relative to a standing waveform. Therefrom an output of mixer 58 is fed to buffer 59 to a driver 60.

With reference to FIG. 6 there is shown a circuit diagram reflecting one form of reduction to practice of the block diagram of FIG. 5.

Figure 7:
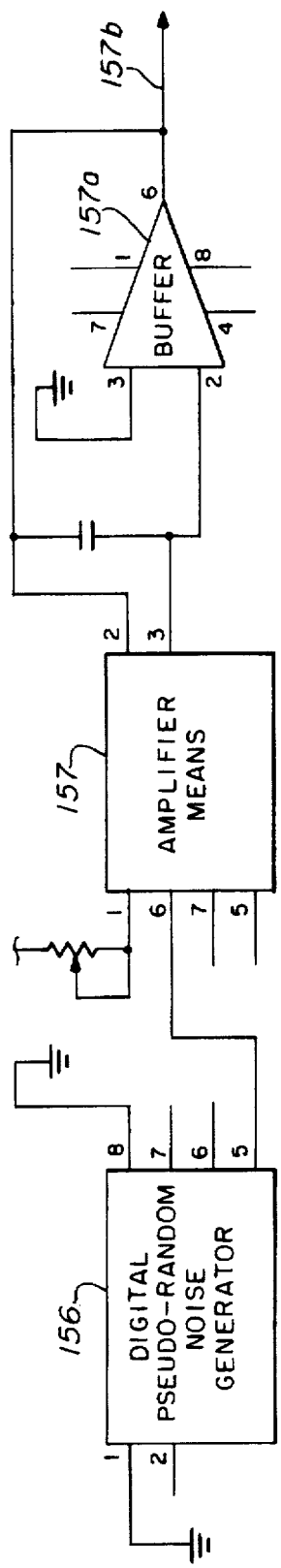
FIG. 7 is a view of an alternate embodiment of FIGS. 5 and 6 showing the use of a digital noise generator in lieu of a random noise generator.

With reference to FIG. 7 is shown an alternate reduction to practice of the circuit of FIG. 5 in which, in lieu of a random noise generator, there is employed a digital pseudorandom noise generator 156 having amplifier 157, buffer 157a with resultant random noise 157b.

Figure 8:
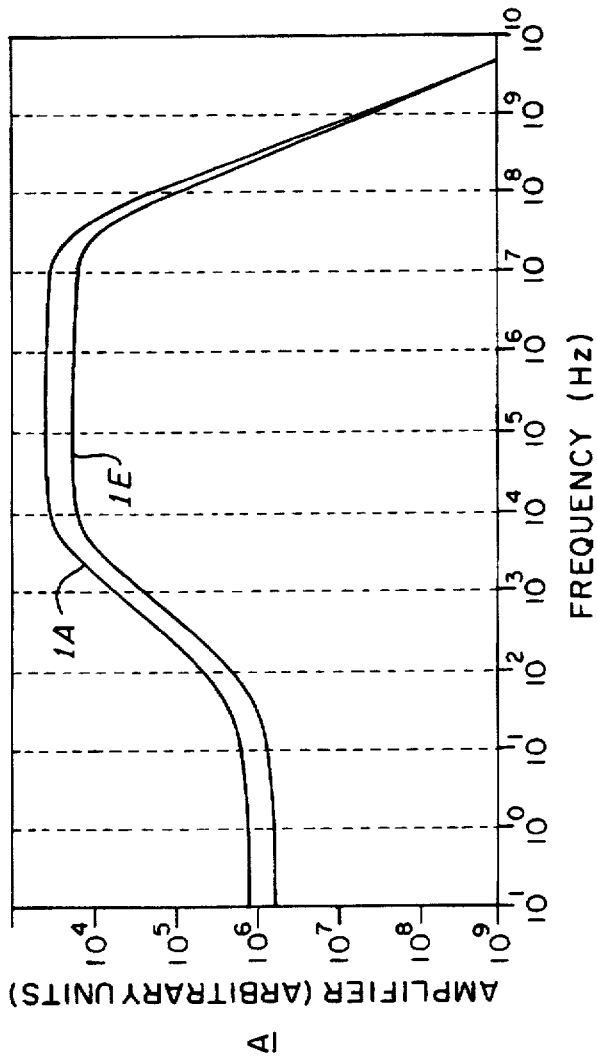
FIG. 8 is a graph which compares output amplitude over a broad frequency spectrum, for use of the irregularly modulated waveform of FIG. 1E of the invention, in relation to use of the prior art unmodulated waveform of FIG. 1A, the latter being characterized by greater power consumption.

With reference to FIG. 8 there is shown a graph of amplitude of PRF waveforms 18 of amplitude A received at tissue level plotted as a function of frequency of the delivered EMF. As may be noted, the waveform of FIG. 1E will produce a spectral density comparable to that produced by the prior-art waveform of FIG. 1A, notwithstanding the fact that the power to produce the irregularly modulated pulsed burst of FIG. 1E is 20 percent less than that required to produce the prior art waveform of FIG. 1A.

Figure 9:
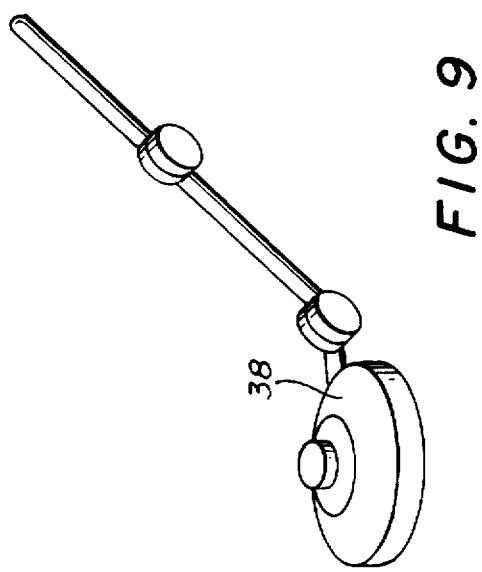
FIG. 9 is a perspective view of a piece of clinical apparatus, namely a body applicator, that may be employed in the practice the instant invention.

With reference to FIG. 9, an electrotherapeutic apparatus is equipped with said applicator 38, which constitutes the means of tissue interface.

EXAMPLES

The following tests have been accomplished to verify the in vivo bio-effects of the above method and system:

Numerous experiments have demonstrated that both weak magnetic and electromagnetic fields are capable of eliciting in vitro and in vivo bioeffects from several different systems. Relatively few studies with cell systems have been recently reported. Although there is available now a substantial literature concerning the bioeffects on cellular systems, tissues and organisms, a reasonable and well accepted mechanism involving biophysical pathways for explaining the coupling of weak magnetic fields to biological systems remains elusive. However controlled magnetic field exposure was accomplished using PRF. We explored the interaction of a cell-free system with a pulsed radiofrequency field of 27.12 MHz, set for random amplitude in the burst portion.

Specifically, we investigated the effects of magnetic fields on an important component of muscle contraction: $Ca^{2+}$-calmodulin dependent myosin phosphorylation. This phosphorylation requires the presence of a substrate (myosin light chains) and an enzyme (myosin light chain kinase), as well as calcium ions. This enzyme system is well suited to study of mechanisms for the coupling of magnetic fields to biological systems.

Experiments were performed by using myosin light chains and a myosin light chain kinase both isolated from turkey gizzard. Calmodulin was isolated from bovine brain. The reaction mixture adapted from Adelstein contains a 20 mM Hepes buffer, pH 7.0; 5 mM magnesium acetate; 1 mg/ml bovine serum albumin; 0.1% (w/v) Tween 80; 0.5 mm dithiothreitol; 6 µM myosin light chain; 2 µM calmodulin; 30 µM $CaCl_2$; and 2 µM MLCK. The phosphorylation of myosin light chains were carried out in 1.5 ml centrifuge tubes (Eppendorf). The Eppendorf tubes were placed in a plastic chamber which maintained a constant temperature of 37° C., monitored with a thermistor system during all experiments. This chamber was placed in the central area of the applicator. Control assays were run as shams prior or immediately after magnetic field exposure for the same time period in the same EMF setup with the generator turned off. The reaction was initiated by adding 5 µl gamma $^{32}P$ ATP to the reaction medium, and was stopped with 100 µl LSB stopping solution. The extent of phosphorylation was determined using Cherenkov emission by counting gamma $^{32}P$ incorporation into myosin light chains. Phosphorylation was evaluated 6 min. after the initiation of reaction.

RESULTS

One experiment having two runs was performed in a controlled magnetic field environment, using the techniques described above. Each experiment and control group consisted of 6 independent readings. The average data of controlled and exposed to PRF samples are shown in the table below:

|  | Control | MRT 912 | Random |
|---|---|---|---|
| Sample 1 | 64349 ± 2249 | 77075 ± 1214 | 81014 ± 5060 |
| Sample 2 | 65403 ± 1885 | 91092 ± 144 | 85864 ± 1118 |
| Sample 3 | 29939 ± 746 | 33920 ± 1254 | 41203 ± 330 |
| Sample 4 | 136090 ± 3652 | 201068 ± 4978 | 203285 ± 6380 |
| Sample 5 | 31356 ± 1247 | 34702 ± 1697 | 35054 ± 1023 |

These results demonstrate a significant effect on myosin phosphorylation which compares favorably with those observed using other magnetic fields having five times the power requirements.

As such there is obtained a result superior to prior art PRF systems at a substantially reduced power requirement.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. Apparatus for therapeutically treating human body tissue with electromagnetic radiation, said apparatus comprising:
   (a) first generating means for generating a cyclically repetitive signal at a frequency in the range of one to 100 megahertz, said first generating means including means for repetitively interrupting said repetitive signal to define repetitively pulsed bursts of said repetitive signal, wherein the burst-repetition rate is in a range up to 1000 Hertz;
   (b) second generating means for generating an irregular-signal output;
   (c) modulator means connected for response to said irregular-signal output and also connected to modulate said repetitively pulsed bursts of said repetitive signal, thereby to produce an irregularly modulated output signal;
   (d) a body-applicator device responsive to an input-signal voltage to produce electromagnetic output radiation; and
   (e) drive-connection means for supplying said irregularly modulated output signal to said body-applicator device, the level of output radiation from said device when in body-coupled relation to the electromagnetic output radiation from said device being such as to induce in body tissue current voltage amplitudes in the $10^3$:1 range of mA/cm to V/cm.

2. The apparatus of claim 1 in which the first generating means generates a sinusoidal signal as the cyclically repetitive signal.

3. The apparatus of claim 1 in which the first generating means generates a non-sinusoidal signal as the cyclically repetitive signal.

4. The apparatus of claim 1, in which said second generating means includes a random-noise generator.

5. The apparatus of claim 1, in which said second generating means includes a sinusoidal-wave generator.

6. The apparatus of claim 1, in which said second generating means includes a generator of iterated exponentially varying signals.

7. The apparatus of claim 1, in which said second generating means includes a generator of iterated linearly varying signals.

8. The apparatus of claim 1 in which said first generating means generates said cyclically repetitive signal having a frequency of about 27 megahertz.

9. The apparatus of claim 1, in which said second generating means is a generator of irregularly varying signals.

10. Apparatus for therapeutically treating living tissue and cells with electromagnetic radiation, said apparatus comprising:
    (a) a waveform generator generating as an output a succession of electromagnetic pulse signals having a frequency in excess of one megahertz, said succession of pulse signals generated in a succession of high spectral density burst envelopes generated at a frequency of between 0.01 and 1,000 Hertz, said burst envelope having a varying amplitude and a minimum amplitude value not less than one ten-thousandth ($10^{-4}$) of the maximum value thereof; and
    (b) a body-applicator device responsive to the waveform generator output which, when in tissue-coupled or cell-coupled relationship, induces in such tissue or cell voltage amplitudes in the range of from one mV/cm up to a voltage below the motor response level.

11. The apparatus of claim 10, wherein the envelope includes between 100 and 10,000 of such signals for each such burst.

12. The apparatus of claim 10, wherein the waveform generator generates a monopolar pulse burst envelope.

13. The apparatus of claim 10, wherein the waveform generator generates a bipolar pulse burst envelope.

14. The apparatus of claim 10, wherein the waveform generator generates a pulse burst envelope that varies sinusoidally.

15. The apparatus of claim 10, wherein the waveform generator generates a pulse burst envelope that is randomly varying.

16. The apparatus of claim 10, wherein the waveform generator generates a pulse burst envelope that is exponentially varying.

17. The apparatus of claim 10, wherein the waveform generator generates a pulse burst envelope that is linearly varying.

18. The apparatus of claim 10, wherein the waveform generator generates a pulse signal that is a sinusoidal waveform.

19. The apparatus of claim 10, wherein the waveform generator generates a pulse signal that is a rectangular waveform.

20. The apparatus of claim 10, wherein the waveform generator generates a pulse signal that is a jagged pulse waveform.

21. The apparatus of claim 10, wherein the waveform generator generates a pulse signal that is a non-sinusoidal waveform.

22. The apparatus of claim 10, wherein the waveform generator generates a pulse signal that is a multi-frequency waveform.

23. The method of therapeutically treating human body tissue, using a body-applicator device which responds to an input signal voltage to produce electromagnetic output radiation, which method comprises the steps of:
    (a) generating a cyclically repetitive signal at a frequency in the range of one to 100 megahertz, said repetitive signal being repetitively interrupted to define repetitively pulsed bursts of said repetitive signal, wherein the burst-repetition rate is in a range up to 1000 Hertz;
    (b) generating an irregular signal and using the same to modulate said repetitively pulsed bursts, thereby producing an irregularly modulated output signal; and (c) using said output signal to drive said body-applicator device in body-coupled relation to the electro-magnetic output radiation from said device, the level of output radiation being such as to induce in body tissue voltage amplitudes in the $10^{-3}$:1 range of mA/cm to V/cm.

24. The method of claim 23 further including the step of generating a sinusoidal cyclically repetitive signal.

25. The method of claim 23 further including the step of generating a non-sinusoidal cyclically repetitive signal.

26. The method of claim 23 further including the step of generating a sinusoidally varying signal as the irregular signal.

27. The method of claim 23 further including the step of generating a randomly varying signal as the irregular signal.

28. The method of claim 23 further including the step of generating an exponentially varying signal as the irregular signal.

29. The method of claim 23 further including the step of generating a linearly varying signal as the irregular signal.

30. The method of claim 23 further including the step of generating a time-varying function as the irregular signal of step (b); said time-varying function having a spectral density greater than the spectral density of a pulse burst of step (a) whenever the cyclically repetitive signal of step (a) is sinusoidal.

31. The method of claim 23 further including the step of generating a sinusoidally varying signal as the irregular signal of step (b).

32. The method of claim 23 further including the step of generating the cyclically repetitive signal of step (a) at a frequency of about 27 megahertz.

33. The method of claim 23 further including the step of generating a cyclically repetitive signal in step (a) that is bipolar.

34. The method of claim 23 further including the step of generating a cyclically repetitive signal in step (a) that is a multi-frequency signal.

\* \* \* \* \*